United States Patent
Lim et al.

(10) Patent No.: US 10,463,913 B2
(45) Date of Patent: *Nov. 5, 2019

(54) DEVICE FOR ANALYZING ATHLETIC POSTURE AND METHOD FOR GENERATING ANALYZING INFORMATION FOR ATHLETIC POSTURE

(71) Applicant: GOLFZON CO., LTD., Daejeon (KR)

(72) Inventors: Kang Yoon Lim, Daejeon (KR); Min Ki Park, Daegu (KR); Jeong Soo Lee, Daejeon (KR)

(73) Assignee: GOLFZON CO., LTD., Daejeon (KR)

( * ) Notice: Subject to any disclaimer, the term of this patent is extended or adjusted under 35 U.S.C. 154(b) by 274 days.

This patent is subject to a terminal disclaimer.

(21) Appl. No.: 15/503,400

(22) PCT Filed: Aug. 12, 2015

(86) PCT No.: PCT/KR2015/008453
§ 371 (c)(1),
(2) Date: Feb. 12, 2017

(87) PCT Pub. No.: WO2016/024814
PCT Pub. Date: Feb. 18, 2016

(65) Prior Publication Data
US 2017/0232295 A1    Aug. 17, 2017

(30) Foreign Application Priority Data

Aug. 12, 2014   (KR) .................. 10-2014-0104218

(51) Int. Cl.
*A63B 24/00*    (2006.01)
*A61B 5/103*    (2006.01)
(Continued)

(52) U.S. Cl.
CPC ........ *A63B 24/0006* (2013.01); *A61B 5/1036* (2013.01); *A63B 69/3667* (2013.01);
(Continued)

(58) Field of Classification Search
CPC . A63B 24/0006; A61B 5/0033; A61B 5/1036; A61B 5/1074; A61B 5/4561; A61B 5/743; A63B 69/3667
See application file for complete search history.

(56) References Cited

U.S. PATENT DOCUMENTS 5,344,323 A * 9/1994 Burns .................... A63B 69/00
434/247
5,885,229 A * 3/1999 Yamato ................ A61B 5/1038
600/587

(Continued)

FOREIGN PATENT DOCUMENTS

JP          07-231968 A     9/1995
KR   10-2002-0023720 A     3/2002
(Continued)

OTHER PUBLICATIONS

International Search Report for PCT/KR2015/008453 dated Nov. 16, 2015 from Korean Intellectual Property Office.

*Primary Examiner* — Xuan M Thai
*Assistant Examiner* — Sadaruz Zaman
(74) *Attorney, Agent, or Firm* — Revolution IP, PLLC

(57) ABSTRACT

Disclosed is an athletic posture analysis device including a pressure sensor plate for measuring the distribution of pressure applied to each of the feet of a user who performs an athletic action by the weight of the user, a display device for displaying athletic posture analysis information of the user, and a controller for performing control so as to specify the size and position of each of the feet of the user using information measured by the pressure sensor plate, to map a predetermined foot image, and to display the mapped foot (Continued)

image and the information regarding the distribution of pressure applied to each of the feet of the user in an overlapping fashion through the display device.

11 Claims, 10 Drawing Sheets

(51) Int. Cl.
  *A63B 69/36* (2006.01)
  *A63B 71/06* (2006.01)
(52) U.S. Cl.
  CPC ...... *A63B 71/0622* (2013.01); *A61B 2503/10* (2013.01); *A63B 2069/367* (2013.01); *A63B 2220/56* (2013.01)

(56) References Cited

U.S. PATENT DOCUMENTS

| | | | |
|---|---|---|---|
| 7,503,858 B2* | 3/2009 | Cameron | A63B 24/0003 473/407 |
| 2004/0219498 A1* | 11/2004 | Davidson | A63B 69/00 434/247 |
| 2006/0194178 A1* | 8/2006 | Goldstein | A63B 24/0003 434/252 |
| 2008/0214360 A1* | 9/2008 | Stirling | A61B 5/1038 482/9 |
| 2008/0242437 A1* | 10/2008 | Taylor | A63B 24/0021 473/269 |
| 2009/0204360 A1* | 8/2009 | Ridenour | A61B 5/225 702/139 |
| 2011/0054358 A1 | 3/2011 | Kim et al. | |
| 2011/0260890 A1* | 10/2011 | Larsen | A63B 69/3667 341/20 |
| 2013/0223707 A1* | 8/2013 | Stephenson | A63B 24/0003 382/128 |

FOREIGN PATENT DOCUMENTS

| | | |
|---|---|---|
| KR | 10-0375712 B1 | 3/2003 |
| KR | 10-2003-0065778 A | 8/2003 |
| KR | 10-0393352 B1 | 8/2003 |
| KR | 10-2007-0013395 A | 1/2007 |
| KR | 10-1274114 B1 | 6/2013 |
| KR | 10-1504538 B1 | 3/2015 |

* cited by examiner

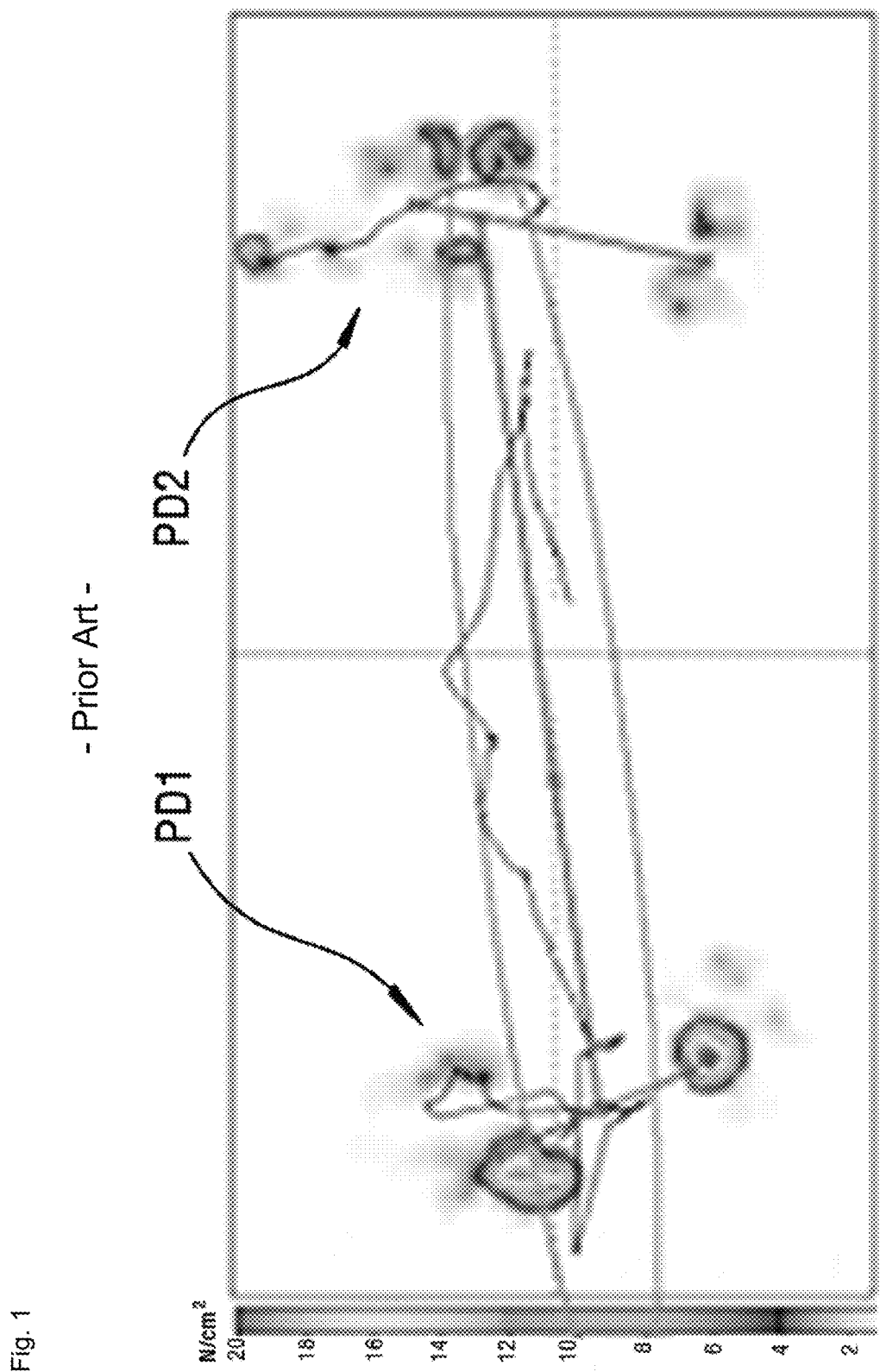
Fig. 1 - Prior Art -

[Fig. 2]
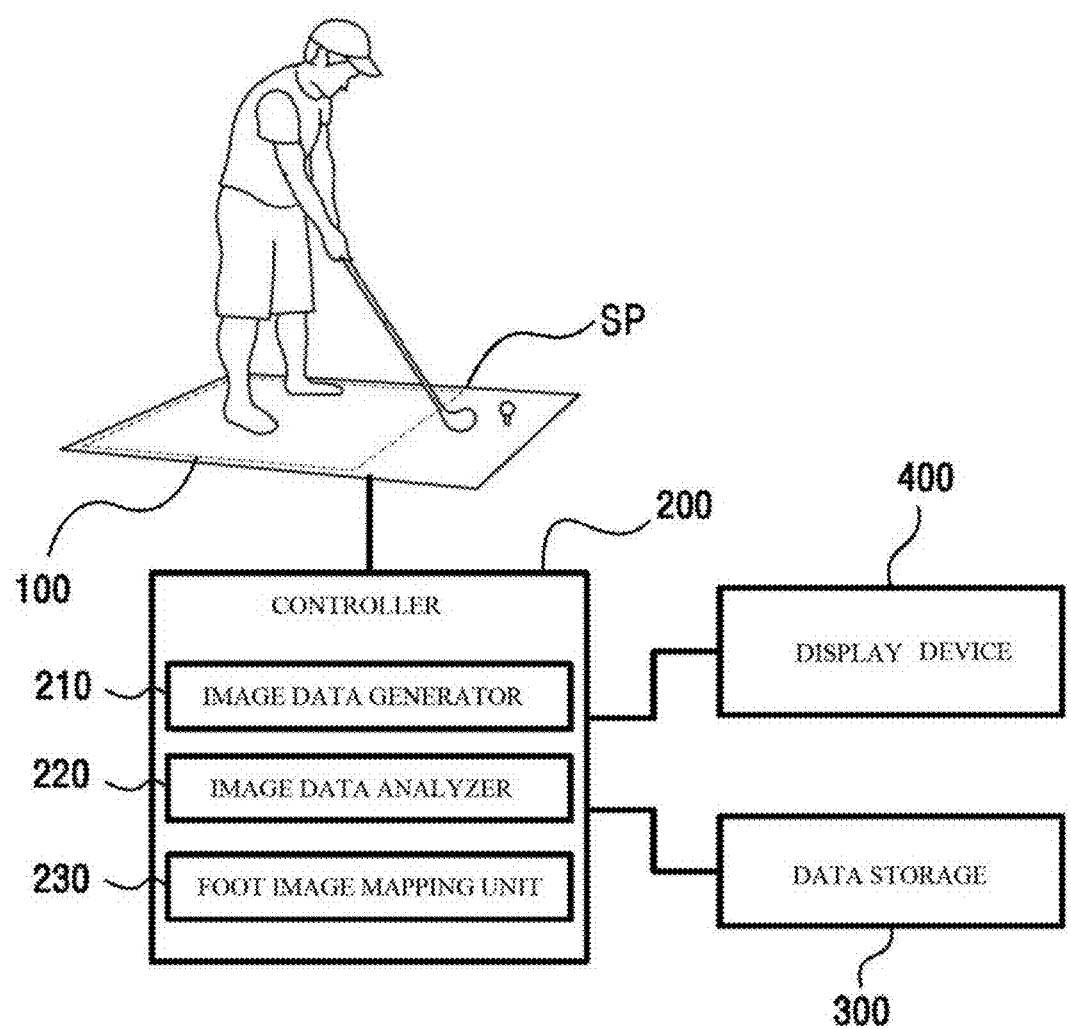

[Fig. 3]
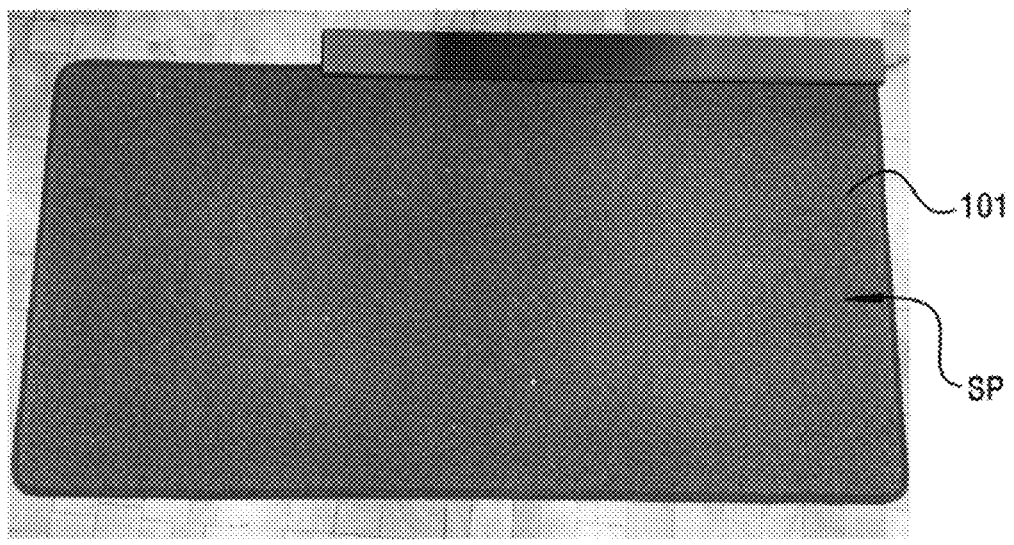
(a)
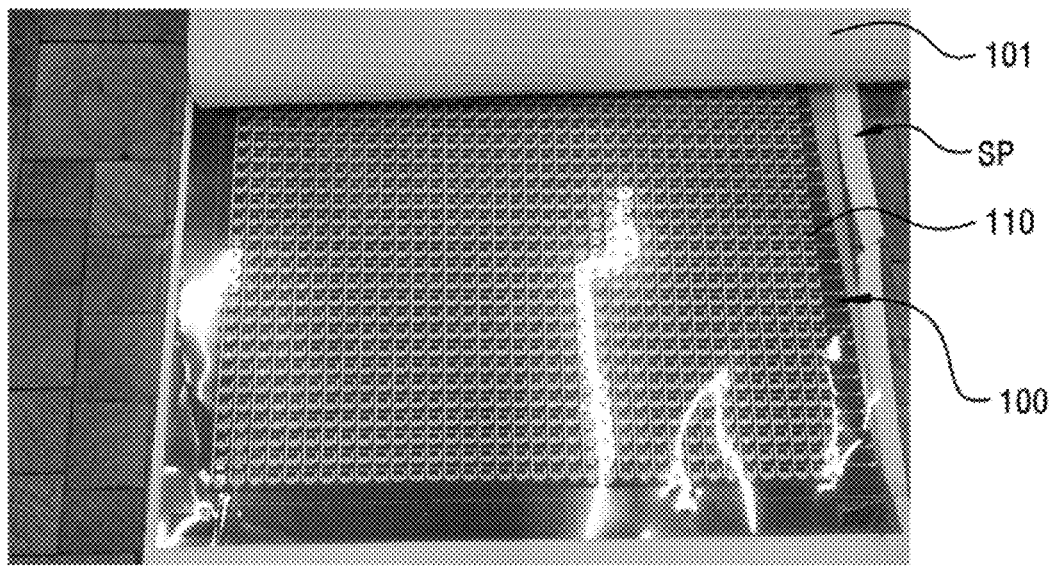
(b)

[Fig. 4]
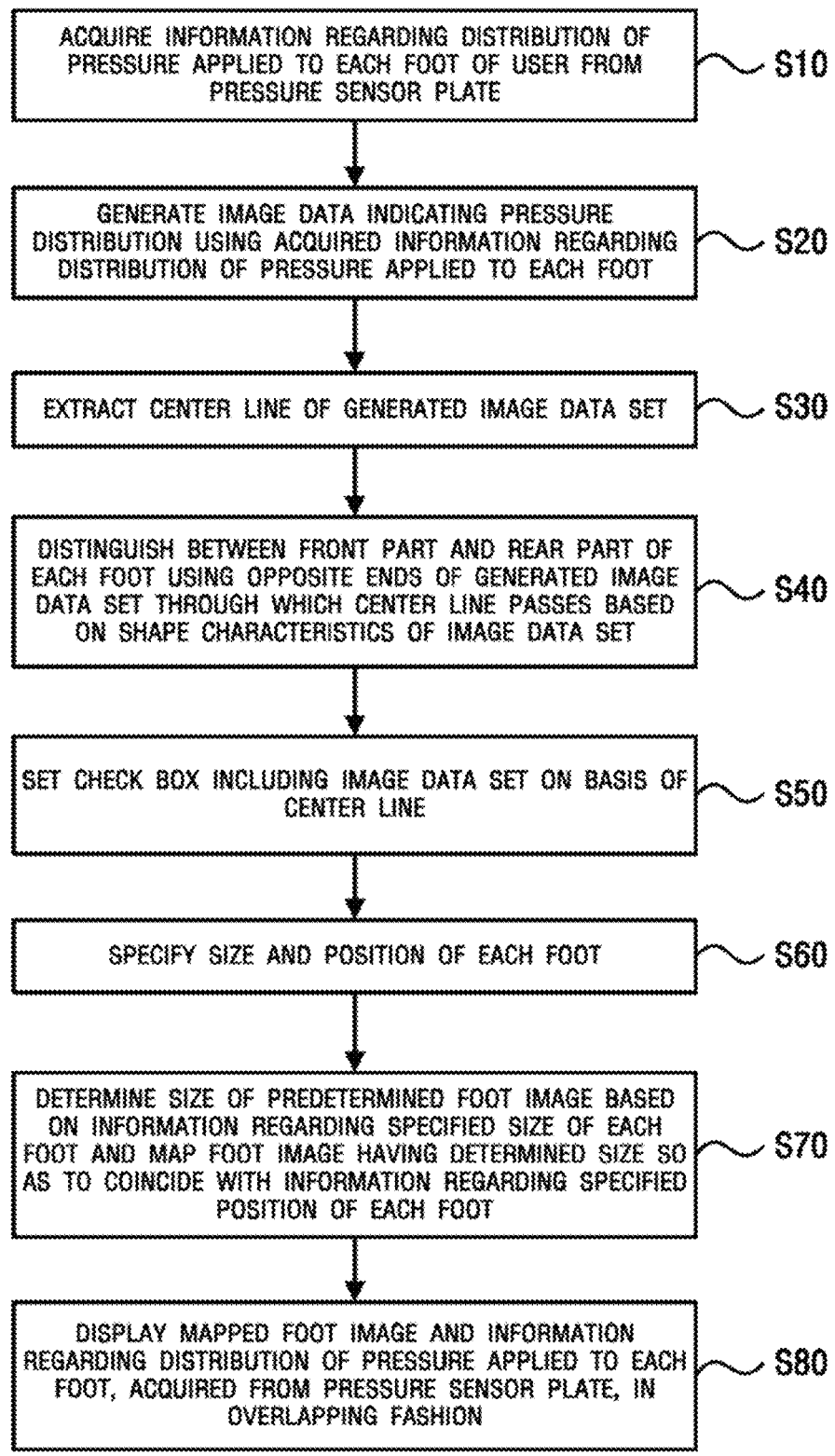

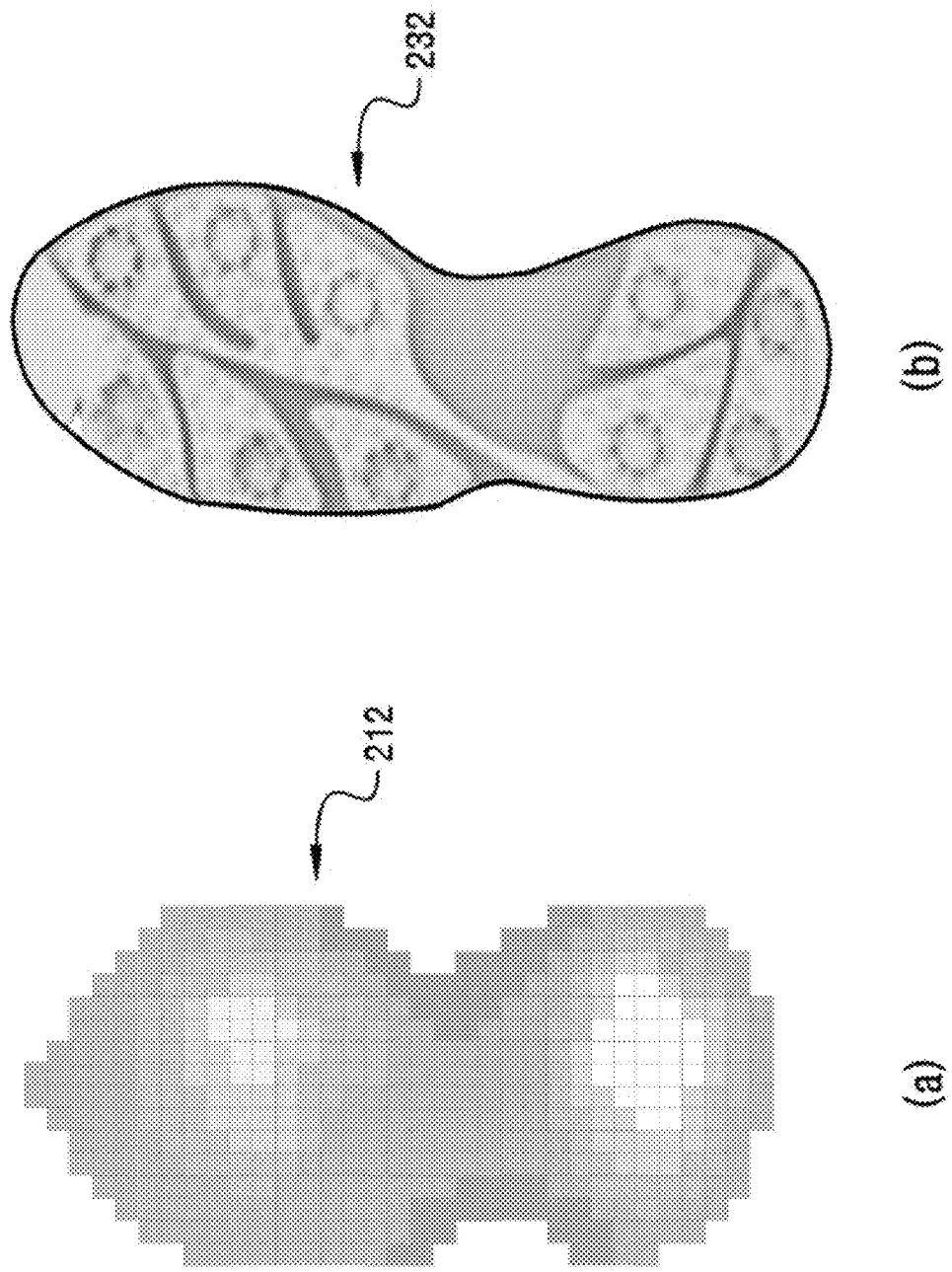
[Fig. 5]

[Fig. 6]
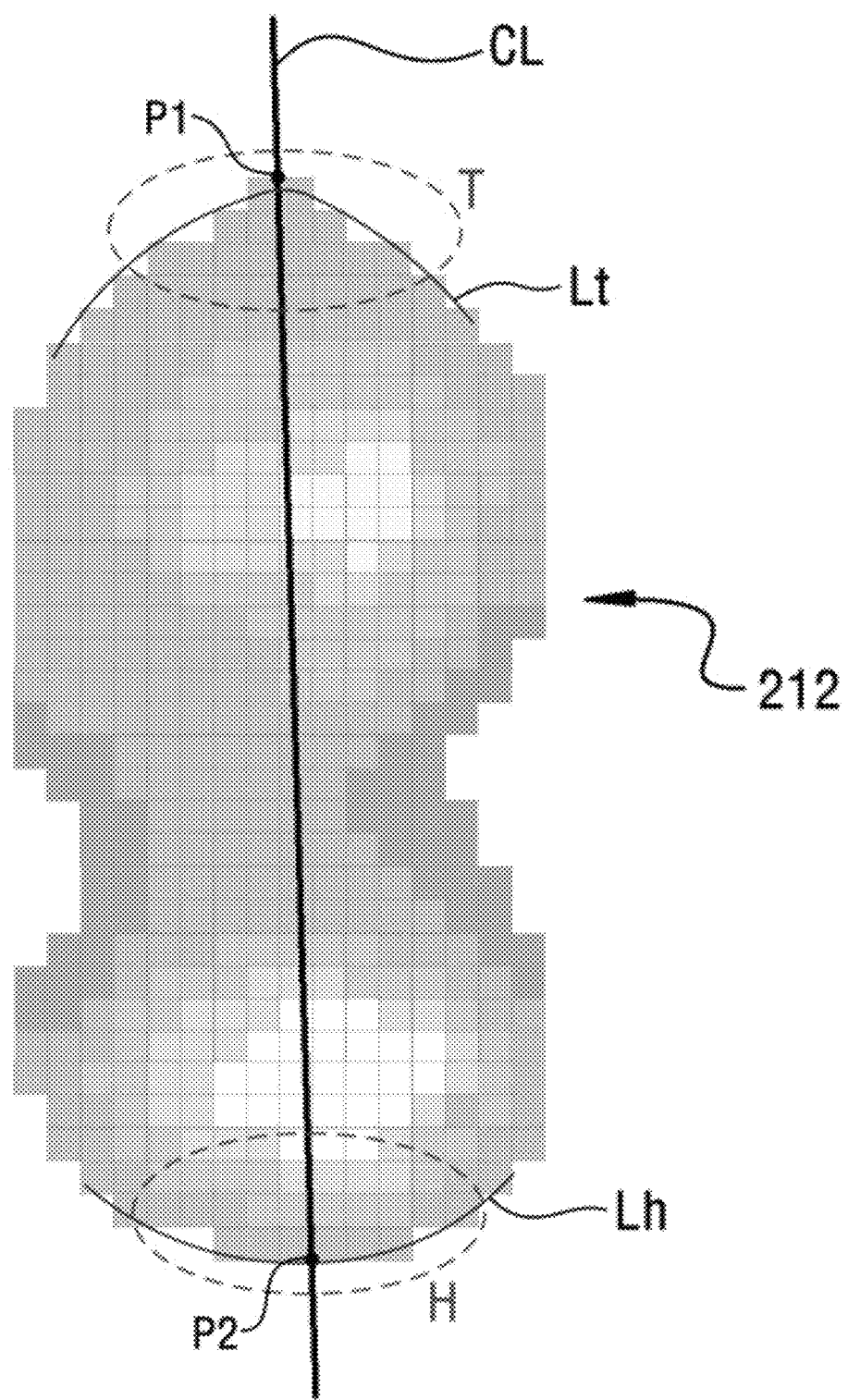

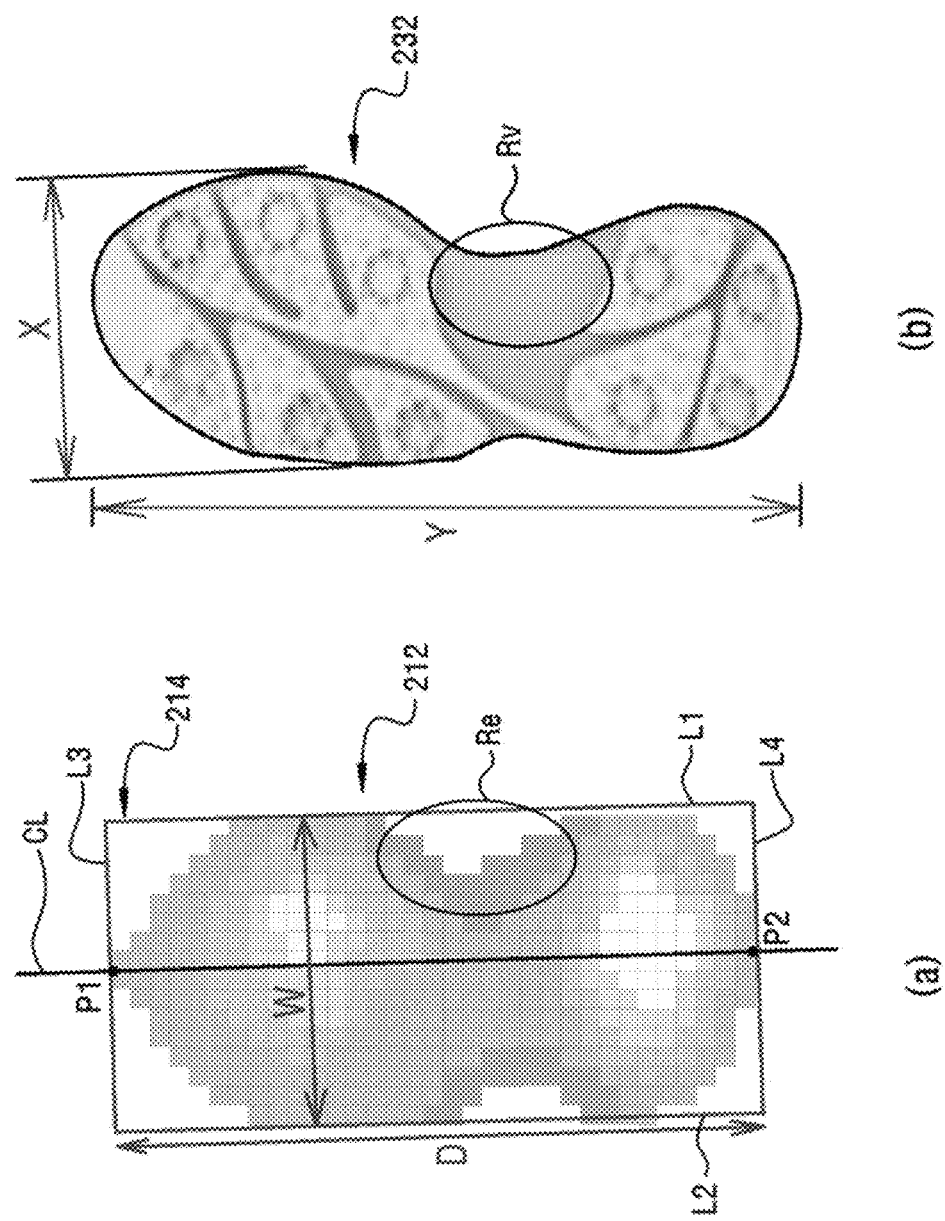

[Fig. 8]
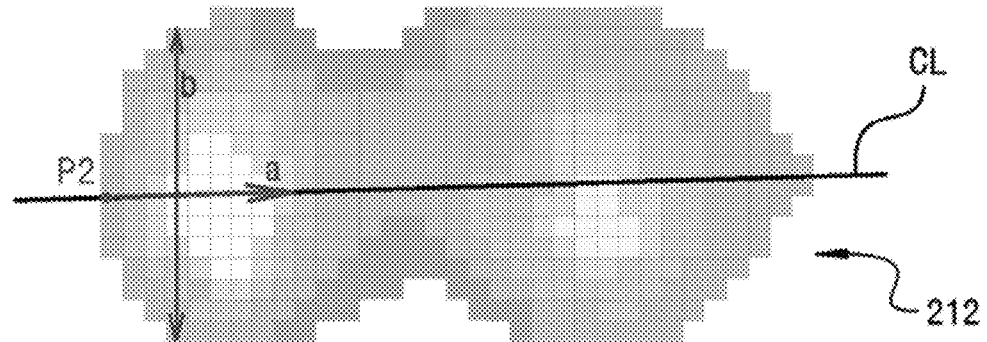
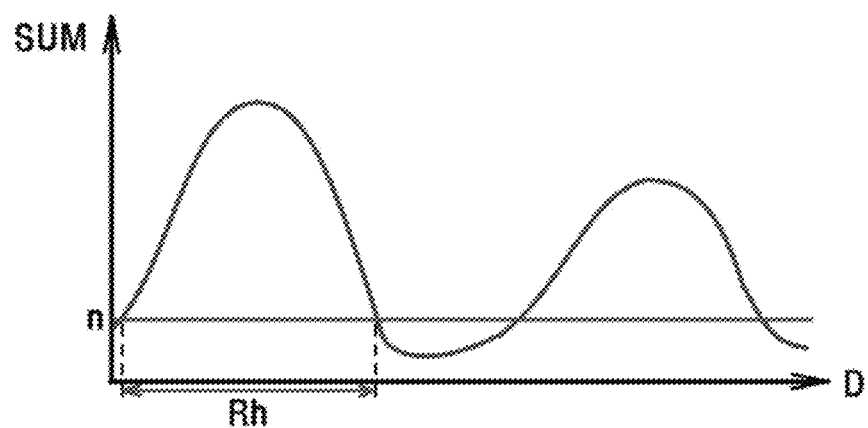

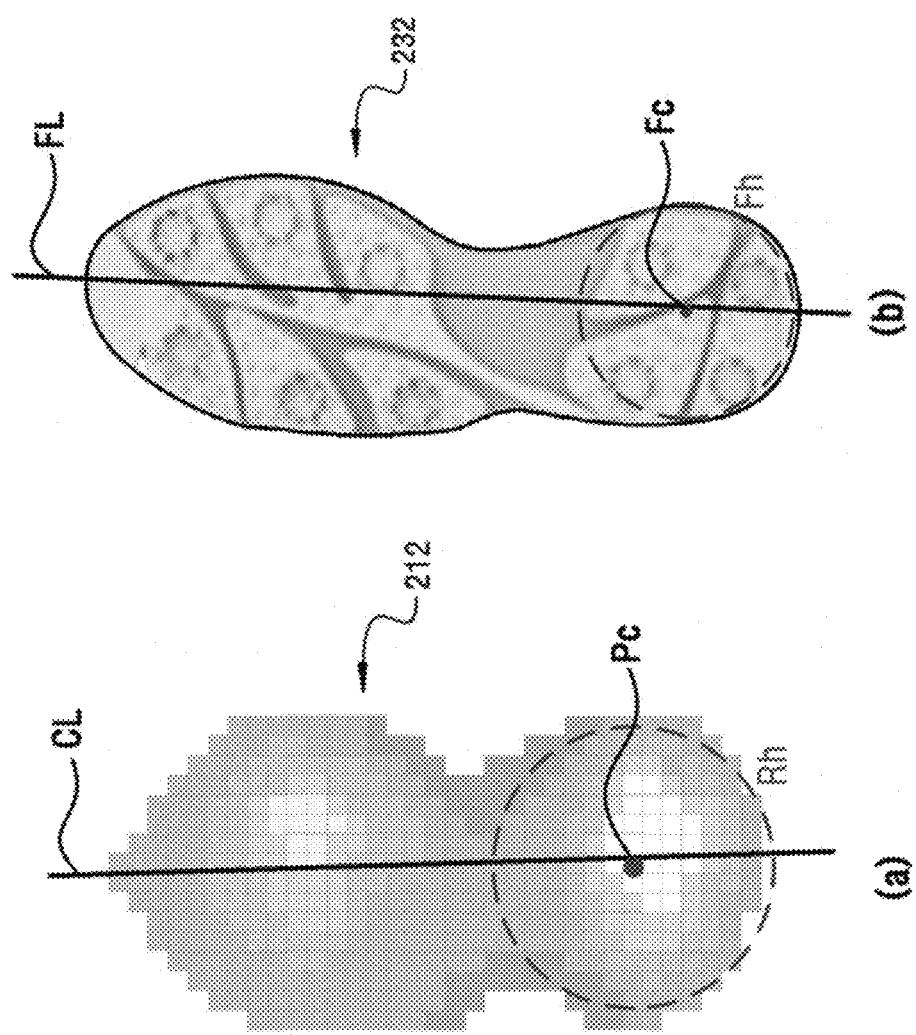
[Fig. 9]

[Fig. 10]
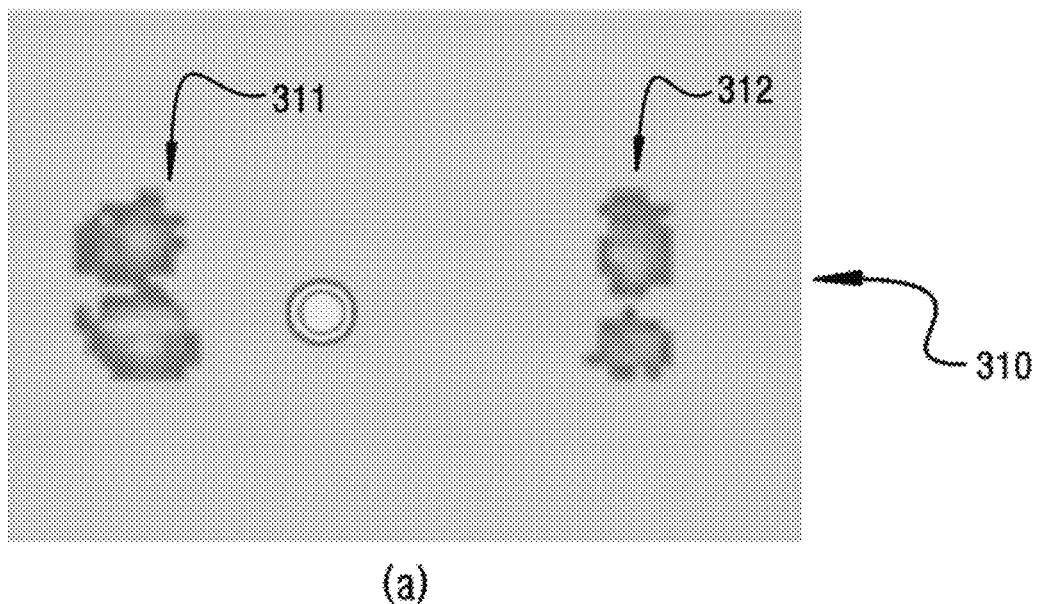
(a)
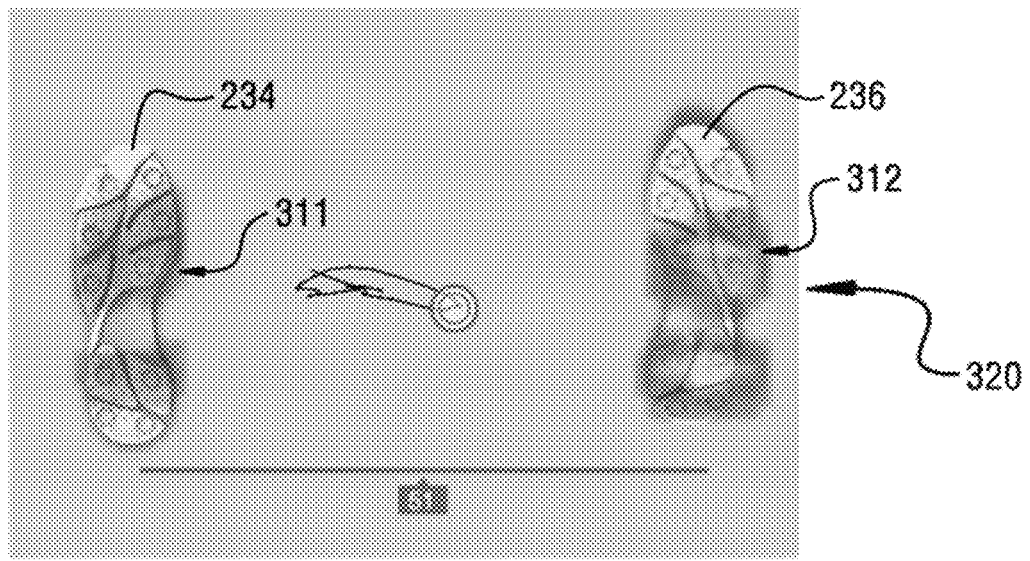
(b)

DEVICE FOR ANALYZING ATHLETIC POSTURE AND METHOD FOR GENERATING ANALYZING INFORMATION FOR ATHLETIC POSTURE

CROSS REFERENCE TO PRIOR APPLICATIONS

This application is a National Stage Application of PCT International Patent Application No. PCT/KR2015/008453 filed on Aug. 12, 2015, under 35 U.S.C. § 371, which claims priority to Korean Patent Application No. 10-2014-0104218 filed on Aug. 12, 2014, which are all hereby incorporated by reference in their entirety.

TECHNICAL FIELD

The present invention relates to an athletic posture analysis device and a method of generating athletic posture analysis information, and more particularly to an athletic posture analysis device and a method of generating athletic posture analysis information that are capable of analyzing an athletic posture, e.g. a golf swing posture, generating appropriate information regarding the athletic posture, and providing the generated information to a user.

BACKGROUND ART

With the great growth of sensor-related technology and sensing data analysis technology in recent years, there have been developed various kinds of analysis devices that are capable of sensing and analyzing an athletic posture of a user using updated sensing technology and analysis technology based thereon to accurately and precisely diagnose problems with the athletic posture of the user, to generate useful information necessary to correct the athletic posture of the user, and to provide the same to the user.

In particular, for golf, among various kinds of sports, it is very difficult to accurately assume a golf swing posture. In addition, problems tend to persist despite extensive practice. For these reasons, people correct their golf swing posture while constantly taking lessons from golf experts. In this way, golf swing practice is performed.

However, correcting the golf swing posture while constantly taking lessons from golf experts is limited in terms of cost and place (practice and lessons are only possible at golf driving ranges). Consequently, various kinds of golf swing posture analysis devices are under development, since the golf swing posture analysis devices are advantageous in terms of cost and place.

In particular, there has been frequently used an analysis device that analyzes the change in load applied to each of the feet of a golfer when the golfer takes a golf swing and provides information regarding analysis of the change in weight shift of the user. Examples of the analysis device that analyzes the change in weight shift of a golfer when the golfer takes a golf swing and provides analysis information are disclosed in Korean Registered Patent No. 10-0393352 and Japanese Patent Application Publication No. 1995-231968.

FIG. 1 is a view showing an example of information regarding analysis of the change in weight shift of a user according to a user's golf swing, generated by a conventional athletic posture analysis device.

Marks shown in the left part and the right part of FIG. 1 indicate the distribution of pressure applied to the feet of the user by the weight of the user when the user takes a swing in the state of standing on a foot plate provided with a pressure sensor.

Most information regarding analysis of the change in weight shift of the user provided by golf swing posture analysis devices that are disclosed as the conventional art or sold as products is provided as shown in FIG. 1.

The information regarding the distribution of pressure applied to the feet of the user by the weight of the user, as shown in FIG. 1, indicates how the load is applied to the left foot and the right foot of the user and how the load is changed in accordance with a user's swing. The above information is provided to the user. In FIG. 1, PD1 indicates the distribution of pressure applied to the left foot of the user by the weight of the user, and PD2 indicates the distribution of pressure applied to the right foot of the user by the weight of the user.

As can be seen from the information regarding the analysis of the change in weight shift of the user, however, it is difficult for the user to know the regions of the left foot and the right foot to which the weight of the user is applied, how much weight of the user is applied thereto, and how pressure is distributed, before a golf expert provides an explanation to the user. Consequently, the conventional athletic posture analysis device, which provides the above-mentioned analysis information, is used merely as a means for assisting golf experts in providing lesson information, and has limitations in use as a personal athletic posture analysis device or an athletic posture analysis device for home use.

Furthermore, the analysis information shown in FIG. 1 is difficult for the user to easily recognize. As a result, it is difficult for the user to reliably accept the analysis information. In addition, it is difficult for the user to recognize problems with the athletic posture of the user and to find solutions thereto. That is, it is difficult for the user to confidently recognize problems with the athletic posture of the user and find solutions thereto.

DISCLOSURE

Technical Problem

The present invention provides an athletic posture analysis device and a method of generating athletic posture analysis information that are capable of very intuitively and visibly displaying analysis information in the case in which analysis of the change in weight shift of a user according to an athletic posture, e.g. a golf swing posture, is needed, thereby solving the above problems with the conventional art, and that are capable of enabling the user to easily recognize problems with the athletic posture of the user and to easily find the solution thereto.

Technical Solution

In accordance with an aspect of the present invention, the above and other objects can be accomplished by the provision of an athletic posture analysis device for analyzing an athletic posture taken by a user who stands on a foot plate, the athletic posture analysis device including a pressure sensor plate provided at the foot plate for measuring the distribution of pressure applied to each of the feet of the user, who performs an athletic action, by the weight of the user, a display device for displaying athletic posture analysis information of the user, and a controller for performing control so as to specify the size and position of each of the feet of the user using information regarding the distribution of pressure applied to each of the feet of the user, measured by the pressure sensor plate, to map a predetermined foot image such that the size and position of the foot image coincide with the specified size and position of each of the feet of the user, and to display the mapped foot image and the information regarding the distribution of pressure applied to each of the feet of the user in an overlapping fashion through the display device.

In accordance with another aspect of the present invention, there is provided a method of analyzing an athletic posture taken by a user who stands on a foot plate to generate athletic posture analysis information, the method including specifying the size and position of each of the feet of the user using information regarding the distribution of pressure applied to each of the feet of the user by the weight of the user, measured by a pressure sensor plate provided at the foot plate for measuring the distribution of pressure applied to each of the feet of the user, who performs an athletic action, by the weight of the user, mapping a predetermined foot image such that the size and position of the foot image coincide with the specified size and position of each of the feet of the user, and displaying the mapped foot image and the information regarding the distribution of pressure applied to each of the feet of the user, measured by the pressure sensor plate, in an overlapping fashion.

Advantageous Effects

The athletic posture analysis device and the method of generating athletic posture analysis information according to the present invention are capable of very intuitively and visibly displaying analysis information in the case in which analysis of the change in weight shift of a user according to an athletic posture, e.g. a golf swing posture, is needed and are capable of enabling the user to easily recognize problems with the athletic posture of the user and to easily find the solution thereto.

DESCRIPTION OF DRAWINGS

FIG. 1 is a view showing an example of user's athletic posture analysis information that is provided by a conventional athletic posture analysis device;

FIG. 2 is a block diagram showing the construction of an athletic posture analysis device according to an embodiment of the present invention;

(a) of FIG. 3 is a view showing an embodiment example of a foot plate, on which a user stands to take an athletic posture as shown in FIG. 2, and (b) of FIG. 3 is a view showing an embodiment example of a pressure sensor plate provided under a cover of the foot plate;

FIG. 4 is a flowchart showing a method of generating athletic posture analysis information according to an embodiment of the present invention;

(a) of FIG. 5 is a view showing an example of a grayscale image, indicating the distribution of pressure applied to each of the feet of the user by the weight of the user, generated by an image data generator of a controller of the athletic posture analysis device according to the embodiment of the present invention, and (b) of FIG. 5 is a view showing an example of a foot image that is mapped by a foot image mapping unit of the controller in accordance with the analysis of image data regarding the distribution of pressure applied to each of the feet of the user;

FIG. 6 is a view illustrating a method of extracting a center line from an image data set regarding the distribution of pressure applied to each of the feet of the user and distinguishing between the front part and the rear part of each of the feet using the athletic posture analysis device according to the embodiment of the present invention;

FIG. 7 is a view illustrating a method of setting a check box with respect to the image data set regarding the distribution of pressure applied to each of the feet of the user to specify the size of each of the feet using the athletic posture analysis device according to the embodiment of the present invention;

FIG. 8 is a view illustrating an example of a method of specifying a heel region of each of the feet from the image data set regarding the distribution of pressure applied to each of the feet of the user using the athletic posture analysis device according to the embodiment of the present invention;

FIG. 9 is a view illustrating an example of a method of mapping a foot image based on the size and position of each of the feet specified from the image data set regarding the distribution of pressure applied to each of the feet of the user using the athletic posture analysis device according to the embodiment of the present invention; and (a) of FIG. 10 is a view showing only information regarding the distribution of pressure applied to each of the feet of the user without mapping the foot image, and (b) of FIG. 10 is a view showing the case in which the foot image mapped by the foot image mapping unit and the information regarding the distribution of pressure applied to each of the feet of the user are displayed in an overlapping fashion.

BEST MODE

Exemplary embodiments of an athletic posture analysis device and a method of generating athletic posture analysis information according to the present invention will be described in detail with reference to the accompanying drawings.

First, the construction of an athletic posture analysis device according to an embodiment of the present invention will be described with reference to FIG. 2.

The athletic posture analysis device according to the embodiment of the present invention is configured to analyze the change in weight shift of a user according to the athletic posture of the user and to provide information regarding such analysis. In particular, the athletic posture analysis device according to the embodiment of the present invention is useful for providing information regarding analysis of the change in weight shift of a user in a golf swing. The athletic posture analysis device according to the embodiment of the present invention is applicable to the analysis of various athletic postures that require analysis of the change in weight shift of a user, besides golf.

Hereinafter, a description will be given of the provision of information regarding the change in weight shift of a user in a golf swing using the athletic posture analysis device according to the embodiment of the present invention and a method of generating athletic posture analysis information according to an embodiment of the present invention.

As shown in FIG. 2, the athletic posture analysis device according to the embodiment of the present invention may include a pressure sensor plate 100, a controller 200, a data storage 300, and a display device 400.

The pressure sensor plate 100 is a device that is provided at a foot plate SP, on which a user stands to take an athletic posture, e.g. a golf swing posture, to measure the distribution of pressure applied to the feet of a user by the weight of the user.

In the conventional art, a load cell is usually used to measure the weight shift of a user. In the athletic posture analysis device according to the embodiment of the present invention, the pressure sensor plate 100 includes a plurality of pressure sensors arranged in a matrix fashion, as shown in FIGS. 3(a) and 3(b). Preferably, therefore, it is possible for each of the pressure sensors to accurately measure the pressure applied to the feet of the user by the weight of the user.

(a) of FIG. 3 is a view showing an embodiment example of the foot plate SP, on which the user stands to take an athletic posture as shown in FIG. 2, and (b) of FIG. 3 is a view showing an embodiment example of the pressure sensor plate 100, which is provided under a cover 101 of the foot plate SP.

As shown in (b) of FIG. 3, the pressure sensor plate 100 may include a plurality of pressure sensors 110, such as force sensing resistors (FSRs). The FSRs may be arranged in a matrix fashion to constitute the pressure sensor plate 100.

Each of the pressure sensors 110 of the pressure sensor plate 100 measures the pressure applied to each of the feet of the user depending on the athletic posture of the user, and transmits measurement information to the controller 200.

The controller 200 performs control so as to generate information regarding the distribution of pressure applied to the feet of the user by the weight of the user using the measurement information, received from the pressure sensor plate 100, and to display the generated information through the display device 400.

The athletic posture analysis device according to the embodiment of the present invention is configured to very intuitively and visibly display information regarding the distribution of pressure applied to the feet of the user by the weight of the user, measured by the pressure sensor plate 100, through the display device. To this end, the controller 200 performs control so as to specify the size and position of each of the feet of the user using the measurement information, received from the pressure sensor plate, to map a predetermined foot image, and to display the mapped foot image and information regarding the distribution of pressure applied to the feet of the user in an overlapping fashion.

In order to perform the above function, as shown in FIG. 2, the controller 200 may include an image data generator 210, an image data analyzer 220, and a foot image mapping unit 230.

The image data generator 210 performs a function of generating data of an image configured to be easy to analyze, e.g. a grayscale image, indicating the distribution of pressure applied to each of the feet of the user, measured by the pressure sensor plate 100.

The image data analyzer 220 performs a function of analyzing the image data, generated by the image data generator 210, to specify information regarding the size and position of each of the feet of the user standing on the pressure sensor plate 100.

The foot image mapping unit 230 performs a function of mapping a predetermined foot image, stored in the data storage 300 (which may store various kinds of images, such as an image indicating the sole of each shoe and an image indicating the sole of each of the feet, in advance), so as to coincide with the size and position of each of the feet of the user, specified by the image data analyzer 220.

The functions of the image data generator 210, the image data analyzer 220, and the foot image mapping unit 230 will be described below in more detail.

Meanwhile, the data storage 300, shown in FIG. 2, is a component for storing data that are necessary for the controller 200 to perform control so as to perform information analysis and mapping and for the display device 400 to display athletic posture analysis information.

The display device 400 is a component for displaying athletic posture analysis information under the control of the controller 200.

Hereinafter, a method of generating athletic posture analysis information, performed by the athletic posture analysis device according to the embodiment of the present invention, will be described with reference to FIG. 4, using the components of the block diagram shown in FIG. 2. FIG. 4 is a flowchart showing a method of generating athletic posture analysis information according to an embodiment of the present invention.

When a user takes a golf swing posture on the foot plate provided with the pressure sensor plate shown in FIG. 3 in order to take a golf swing, each of the pressure sensors of the pressure sensor plate measures the pressure applied to each of the feet of the user by the weight of the user and transmits measurement information to the controller, whereby the controller acquires information regarding the distribution of pressure applied to each of the feet of the user (S10).

The image data generator of the controller generates image data indicating the distribution of pressure applied to each of the feet of the user using the acquired information regarding the distribution of pressure applied to each of the feet of the user (S20). A detailed example thereof will be described with reference to FIG. 5.

The controller performs control so as to extract a center line from an image data set, generated at step S20 (S30). It is preferable to extract the longest major axis passing through the image data set as the center line. A detailed example thereof will be described with reference to FIG. 6.

Meanwhile, the controller performs control so as to distinguish between the front part and the rear part of each of the feet using opposite ends of the image data set through which the center line passes, extracted at step S30, i.e. using the portions of the center line that intersect the contour of the image data set (S40). The front part and the rear part of each of the feet may be distinguished using shape characteristics of the image data set, or may be distinguished based on data distribution. Details thereof will be described with reference to FIGS. 6 and 7.

Meanwhile, the controller performs control so as to set a check box at the contour of the image data set on the basis of the center line (S50) and to analyze the center line, the check box, and the data distribution of the image data set to specify the size and position of each of the feet (S60). A detailed example of specification of the size and position of each of the feet will be described with reference to FIGS. 7 to 9.

When the size and position of each of the feet are specified from the image data set, indicating the information regarding the distribution of pressure applied to each of the feet of the user, as described above, the controller performs control so as to determine the size of a predetermined foot image based on information regarding the specified size of each of the feet and to map the foot image having the determined size so as to coincide with information regarding the specified position of each of the feet, whereby a foot image having a size and a position corresponding to the image data set may be displayed (S70).

The controller performs control so as to display the mapped foot image and the information regarding the distribution of pressure applied to each of the feet of the user, acquired by the pressure sensor plate, in an overlapping fashion (S80). As a result, it is possible for the user to very intuitively recognize the change in weight shift of the user according to the golf swing posture of the user. A detailed example thereof will be described with reference to FIG. 10.

Hereinafter, the respective steps of the flowchart shown in FIG. 4 will be described in detail with reference to FIGS. 5 to 10.

(a) of FIG. 5 is a view showing an example of a grayscale image, including pixels having brightness values indicating the distribution of pressure applied to each of the feet of the user by the weight of the user, generated by the image data generator of the controller of the athletic posture analysis device according to the embodiment of the present invention, and (b) of FIG. 5 is a view showing an example of a foot image that is mapped by the foot image mapping unit of the controller in accordance with the analysis of image data regarding the distribution of pressure applied to each of the feet of the user.

The image data generator of the controller of the athletic posture analysis device according to the embodiment of the present invention receives values measured by the pressure sensors 110 (see FIG. 3) in the state in which the user stands on the pressure sensor plate 100 (see FIG. 3), and generates data of a grayscale image having pixel values (i.e. brightness values) corresponding to the values measured by the pressure sensors, as shown in (a) of FIG. 5. The brighter portions of an image data set 212 shown in (a) of FIG. 5 are the portions of each of the feet to which higher pressure is applied.

A foot image 232 shown in (b) of FIG. 5 is a predetermined image, and an image indicating the sole of a golf shoe is shown in (b) of FIG. 5. However, various foot images may be set. For example, an image indicating the sole of a bare foot or an image indicating a general sports shoe may also be set.

However, only the design of the foot image 232 shown in (b) of FIG. 5 is set in advance, but the size and position of each of the feet are not set. For this reason, the size and position of each of the feet are specified through analysis of the image data set 212 shown in (a) of FIG. 5, the size and position of the foot image 232 are adjusted so as to coincide with the specified size and position of each of the feet, and the foot image 232 is mapped.

The operation of specifying the size and position of each of the feet, performed by the image data analyzer of the controller of the athletic posture analysis device according to the embodiment of the present invention using image data of each of the feet, will be described in detail with reference to FIGS. 6 to 9.

In the method of specifying the size of each of the feet using the data of the grayscale image, the contour of the image data set may be extracted, the extracted contour may be regarded as the shape of each of the feet, and the width of each of the feet (i.e. the largest length of each of the feet in the lateral direction) may be calculated, whereby the size of each of the feet may be specified.

In addition, the center line of the image data set may be extracted, and the size and position of each of the feet may be specified based on specific criteria, which will be described in detail hereinafter.

In order to specific the size and position of each of the feet using the image data shown in (a) of FIG. 5, it is necessary to extract a center line CL, as shown in FIG. 6, and to distinguish between the front part and the rear part of each of the feet from the image date set 212.

As shown in FIG. 6, the image data analyzer extracts the longest major axis passing through the image data set 212 as the center line CL.

The center line CL may be extracted using a line fitting algorithm, such as a method of least squares or a random sample consensus (RANSAC) algorithm. In consideration of data distribution, the RANSAC algorithm is more preferably used to extract the center line. The RANSAC algorithm is a well-known line fitting algorithm, and therefore a detailed description thereof will be omitted.

The center line CL extracted as described above is a basis for mapping the foot image, a description of which will follow.

Meanwhile, in the case in which the longest major axis passing through the image data set is extracted as the center line CL, as described above, the center line inevitably passes through the front part and the rear part of each of the feet.

Consequently, in the case in which the center line CL is extracted, as described above, opposite ends of the image data set through which the center line CL passes may correspond to the front part and the rear part of each of the feet, and the front part T and the rear part H of each of the feet may be distinguished based on the entire shape of a portion of the image data set 212 adjacent to point P1 and the entire shape of a portion of the image data set 212 adjacent to point P2.

That is, since the portion of the image data set 212 having a gentle slope corresponds to the rear part H of each of the feet, as shown in FIG. 6, the image data analyzer of the present invention may analyze the shape characteristics of the image data set at the opposite ends of the image data set on the basis of the center line CL to distinguish between the front part T and the rear part H of each of the feet.

In FIG. 6, a curved line denoted by Lt and a curved line denoted by Lh are arbitrary curved lines drawn to describe the shape characteristics of the opposite ends of each of the feet. Comparing the curved line Lt with the curved line Lh, it can be seen that the curved line Lh has a larger curvature and that the portion having the curved line Lh corresponds to the rear part of each of the feet. (Since, for most shoes, the rear parts of the shoes are less contoured than the front parts of the shoes in terms of shape characteristics, such shape characteristics are equally applicable to the image data set.)

However, information regarding the distribution of pressure applied to each of the feet of the user may not be perfect depending on the kind of the shoes that the user who stands on the pressure sensor plate 100 (see FIG. 3) wears or the state in which each of the feet of the user pushes the pressure sensor plate. In this case, it may be difficult to distinguish between the front part and the rear part of each of the feet based on the shape characteristics of the image data set.

In an example, in the case in which hobnails or spikes are present in the sole of the shoe, the pressure applied to each of the feet may not be completely transmitted to the pressure sensors. In another example, in the case in which the user takes an athletic posture while lifting toes, the front part of each of the feet may not be completely transmitted to the pressure sensors. As a result, some of the image data may not be completely displayed.

Consequently, the image data analyzer of the present invention may distinguish between the front part and the rear part of each of the feet from the image data set using another method of distinguishing between the front part and the rear part of each of the feet together with the method of distinguishing between the front part and the rear part of each of the feet based on the shape characteristics of the image data set or separately from the method of distinguishing between the front part and the rear part of each of the feet based on the shape characteristics of the image data set.

To this end, the image data analyzer may set a check box 214 at the contour of the image data set 212 on the basis of the center line CL, and may specify the size of each of the feet using the check box.

That is, as shown in FIG. 7(a), the image data analyzer may generate a first vertical line L1 that abuts on the right side of the image data set 212 on the basis of the center line CL and that is parallel to the center line CL, a second vertical line L2 that abuts on the left side of the image data set 212 on the basis of the center line CL and that is parallel to the center line CL, a first horizontal line L3 that abuts on the front side of the image data set 212 and that is perpendicular to the center line CL, and a second horizontal line L4 that abuts on the rear side of the image data set 212 and that is perpendicular to the center line CL in order to set a check box 214 that is defined by the first vertical line L1, the second vertical line L2, the first horizontal line L3, and the second horizontal line L4.

As shown in FIG. 7(a), regions having very small data values (i.e. brightness values or measured pressure values) or no data values exist in the check box 214, in which the image data set 212 is located. For example, the pressure value measured in an inner concave region of each of the feet (a region denoted by Rv in FIG. 7(b)), which is formed based on the structural characteristics of the sole of each of the feet, is small or null. When an image of each of the feet is generated, therefore, the brightness value of the image corresponding to the region of each of the feet is very small or null. The above-mentioned region will be referred to as an "empty region."

One or more empty regions may exist in the image data set indicating the distribution of pressure applied to each of the feet depending on the state of each of the shoes or the posture of each of the feet. In consideration of the structure of each of the feet, the inner concave region of each of the feet is displayed as the largest empty region. In the case in which one or more empty regions are detected in the image data set, therefore, the largest empty region may be determined to be the inner concave region of each of the feet, and the front part and the rear part of each of the feet may be distinguished based thereon. The largest empty region is denoted by Re in the figure.

The image data analyzer of the present invention may detect the empty region Re, and may determine the part of the image data set 212 in which the detected empty region Re is located, or may determine the side of the image data set 212 to which the detected empty region Re is closer on the basis of the center line CL to distinguish between the front part and the rear part of each of the feet.

For example, the image data analyzer may distinguish between the left foot and the right foot from the image data set of the feet of the user. Then, the image data analyzer may detect the empty region from the image data set of each foot and may determine whether the empty region is located at the left side of the image data set or at the right side of the image data set to distinguish between the front part and the rear part of each of the feet. In addition, the image data analyzer may determine whether the empty region is biased to the front part or the rear part of the image data set on the basis of the center line CL to distinguish between the front part and the rear part of each of the feet.

Meanwhile, as described above, the check box 214 may be set on the basis of the center line CL, and the width W of the set check box 214 may be calculated to specify the size of each of the feet. Then, the width X of the foot image 232 shown in FIG. 7(b) may be adjusted to coincide with the width W of the check box 214, whereby it is possible to obtain a foot image having a specified size of each of the feet from the image data.

That is, since, when the width X of the foot image is reduced or magnified so as to coincide with the width W of the set check box, the length Y of the foot image is reduced or magnified accordingly (i.e. since the ratio of X to Y is fixed, the size of the foot image is adjusted when X is adjusted so as to coincide with W), information regarding the width X of the foot image may be specified using the check box 214 of the image data set 212, whereby the size of each of the feet may be specified.

The size of each of the feet may be specified on the basis of the length of the image data set 212 shown in FIG. 7(a), i.e. the length D of the check box 214.

Since the front part of each of the feet may not be completely displayed as the image data depending on the state of the shoe of the user or the posture of each of the feet of the user, as described above, however, the length D of the check box 214 may not reflect the correct value. For this reason, there may be limitations in determining the correct size of each of the feet on the basis of the length D of the check box 214.

Hereinafter, the operation of detecting the heel region of each of the feet in order to specify the position of each of the feet from the image data set 212 will be described.

As described above, the distribution of pressure applied to each of the feet of the user may not be completely displayed depending on the state of the shoe of the user or the posture of each of the feet of the user. Even in this case, the data of the image data set corresponding to the rear part of each of the feet are completely displayed, since most of the weight of the body of the human being is applied to the heel of each of the feet due to the structural characteristics of the body (unless the heel of each of the feet is not lifted in the athletic posture).

Consequently, it is preferable to detect the heel region of each of the feet from the image data set and to specify the position of each of the feet based on the detected heel region of each of the feet.

FIG. 8 is a view illustrating an example of a method of specifying the heel region of each of the feet from the image data set 212.

In order to extract the heel region of each of the feet from the image data set 212, first, it is necessary to distinguish between the front part and the rear part of each of the feet at opposite ends of the image data set 212 through which the center line CL passes, which was described previously with reference to FIGS. 6 and 7.

In the case in which the front part and the rear part of each of the feet are distinguished, as described above, the sum of data values of data arranged from the start point P2 of the rear part of each of the feet in the direction indicated by an arrow a and in the direction indicated by an arrow b is calculated, as shown in FIG. 8.

The calculated sum of the data values is shown as a graph having a pattern shown in FIG. 8.

The distribution of the sum of the data values from the start point P2 of the rear part of each of the feet forms a pattern that is abruptly increased, is abruptly decreased, and is then gradually increased, as shown in the graph of FIG. 8. The reason that the sum of the data values is abruptly decreased is because the data value of the data corresponding to the inner part of each of the feet is very small or null. In the case in which an appropriate value is set as a reference value n, as shown in FIG. 8, the region having the sum of the data values higher than the reference value may be specified as the heel region Rh of each of the feet.

The reference value n may be set as the value at the position at which the graph is started (i.e. the sum of the data values of the data from the start point P2 of the rear part of each of the feet in the direction indicated by the arrow b). The reference value n may also be set as a value having a predetermined offset value applied thereto (for example, a value obtained by adding a value preset as the offset value to the value at the start point P2 may be set as the reference value). In addition, the reference value n may be set as a predetermined value.

After the heel region of each of the feet is specified using the distribution of the sum of the data values, as described above, the image data analyzer of the present invention extracts a center point Pc of the heel region Rh of each of the feet based on the specified heel region of each of the feet, as shown in FIG. 9(a).

The heel region Rh of each of the feet specified from the image data set 212 may be a region set by data located outside the data within the range set based on the reference value n in the graph of FIG. 8, or may be a region that approximates a circle, as shown in FIG. 9.

The center point Pc may be set as the center of gravity of the specified heel region Rh of each of the feet, or may be set as a point that forms the spatial center of the specified heel region Rh of each of the feet.

Meanwhile, it is necessary to specify a heel region Fh of the foot image and a center point Fc of the heel region with respect to the foot image 232 shown in FIG. 9(b). This is information that is preset as the size of the foot image is determined. That is, the above information may be set when the size of the foot image is determined, since information regarding the foot image is predefined and predetermined information.

Extraction of the center line of the image data set 212, shown in FIG. 9(a), was described previously with reference to FIG. 6. Correspondingly, as shown in FIG. 9(b), the longest major axis passing through the foot image 232 is extracted as a center line FL, which is information that is preset as the size of the foot image is determined.

Consequently, the center line CL and the center point Pc of the heel region Rh of each of the feet are extracted from the image data, as described above, whereby information regarding the position of each of the feet may be specified. The foot image mapping unit of the present invention adjusts the center point Fc of the heel region Fh of the foot image 232, the size of which is determined, so as to correspond to the center point Pc of the heel region Rh of each of the feet extracted from the image data, and maps the foot image 232 in the state in which the center line FL of the foot image 232 corresponds to the center line CL extracted from the image data. That is, the foot image is displayed in the state of being adjusted so as to coincide with the size and position of each of the feet specified from the image data.

The controller of the athletic posture analysis device according to the embodiment of the present invention performs control such that the foot image mapped by the foot image mapping unit and the information regarding the distribution of pressure applied to each of the feet of the user, received from the pressure sensor plate, are displayed through the display device in an overlapping fashion.

FIG. 10 shows an example in which the mapped foot image and the information regarding the distribution of pressure applied to each of the feet of the user are displayed in an overlapping fashion, as described above.

(a) of FIG. 10 is a view showing only the information regarding the distribution of pressure applied to each of the feet of the user without mapping the foot image, and (b) of FIG. 10 is a view showing the case in which the foot image mapped by the foot image mapping unit and the information regarding the distribution of pressure applied to each of the feet of the user are displayed in an overlapping fashion.

The left part 311 of athletic posture analysis information 310 shown in (a) of FIG. 10 indicates information regarding the distribution of pressure applied to the left foot of the user by the weight of the user, measured by the pressure sensor plate, and the right part 312 of the athletic posture analysis information 310 indicates information regarding the distribution of pressure applied to the right foot of the user by the weight of the user, measured by the pressure sensor plate.

In addition, athletic posture analysis information 320 shown in (b) of FIG. 10 indicates that a foot image 234 corresponding to the left foot and a foot image 236 corresponding to the right foot are mapped and displayed in the state in which the information 311 regarding the distribution of pressure applied to the left foot of the user and the information 312 regarding the distribution of pressure applied to the right foot of the user are overlapped thereon.

The controller of the athletic posture analysis device according to the embodiment of the present invention may perform control such that the position of the mapped foot image is finely adjusted based on the information regarding the distribution of pressure applied to each of the feet of the user overlapped thereon, whereby athletic posture analysis information is finally displayed.

For example, upon determining that the information regarding the distribution of pressure applied to each of the feet of the user is very far from the mapped foot image or upon determining that the size of the foot image is much smaller or larger than the information regarding the distribution of pressure applied to each of the feet of the user, the controller may perform control such that the size or position of the mapped foot image is finely adjusted so as to correspond to the information regarding the distribution of pressure applied to each of the feet of the user.

In the case in which only the information regarding the distribution of pressure applied to each of the feet of the user is displayed, as shown in (a) of FIG. 10, it is difficult for the user to understand the information regarding the distribution of pressure applied to each of the feet of the user based on the athletic posture of the user without the aid of an expert. In the athletic posture analysis device and the method of generating athletic posture analysis information according to the present invention, however, the foot image is mapped so as to correspond to the foot posture of the user and is displayed in the state in which information regarding the distribution of pressure applied to each of the feet of the user is overlapped thereon, as shown in (b) of FIG. 10, whereby it is possible for the user to easily and intuitively recognize the distribution of pressure applied to each of the feet of the user depending on the foot posture of the user and to easily recognize problems with the athletic posture of the user.

MODE FOR INVENTION

Various embodiments have been described in the best mode for carrying out the invention.

INDUSTRIAL APPLICABILITY

The athletic posture analysis device and the method of generating athletic posture analysis information according to The present invention are applicable to sports-related industries for analyzing athletic postures, such as golf swings, and to learning and training-related industries for analyzing sports actions, performing information processing, and using the results thereof.

The invention claimed is:

1. An athletic posture analysis device for analyzing an athletic posture taken by a user who stands on a foot plate, the athletic posture analysis device comprising:
   a pressure sensor plate provided at the foot plate, the pressures sensor plate having a plurality of pressure sensors configured to measure a distribution of pressure applied to each of feet of the user, who performs an athletic action, by a weight of the user;
   a display configured to display athletic posture analysis information of the user; and
   a controller configured to:
      generate an image data having pixel values corresponding to values measured by the pressure sensor plate;
      extract a longest major axis passing through a generated image data set as a center line, and distinguish between a front part and a rear part of each of the feet using opposite ends of the generated image data set through which the center line passes;
      specify a size of each of the feet by measuring a width of the generated image data set on a basis of the center line, and a position of each of the feet by the distinguished front and rear parts of each of the feet;
      determine a size of a foot image having a predetermined design corresponding to the specified size of each of the feet;
      map the foot image having the determined size to coincide with the specified position of each of the feet; and
      display the mapped foot image through the display.

2. The athletic posture analysis device according to claim 1, wherein the controller is configured to overlap the measured distribution of pressure applied to each of the feet with the mapped foot image and display the overlapped image through the display.

3. The athletic posture analysis device according to claim 1, wherein
   the plurality of pressure sensors are arranged in a matrix fashion, and
   the controller receives values measured by the respective pressure sensors in a state in which the user stands on the pressure sensor plate and generates data of a grayscale image as the data of the image having brightness values based on the values measured by the pressure sensors.

4. The athletic posture analysis device according to claim 1, wherein the controller extracts a contour of the generated image data set and specifies the size and position of each of the feet of the user based on the extracted contour.

5. The athletic posture analysis device according to claim 1, wherein the controller sets a check box at a contour of the image data set on a basis of the center line and specifies the size of each of the feet using a size of the check box, and analyzes a shape of the image data set on the basis of the center line so as to specify a heel region of each of the feet, thereby specifying the information regarding the size and position of each of the feet of the user.

6. A method of analyzing an athletic posture taken by a user who stands on a foot plate to generate athletic posture analysis information, the method comprising:
   measuring, via a pressure sensor plate, a distribution of pressure applied to each of feet of the user, who performs an athletic action, by a weight of the user;
   generating an image data having pixel values corresponding to the values measured by the pressure sensor plate;
   extracting a longest major axis passing through a generated image data set as a center line, and distinguishing between a front part and a rear part of each of the feet using opposite ends of the generated image data set through which the center line passes;
   specifying a size of each of the feet by measuring a width of the generated image data set on a basis of the center line, and a position of each of the feet by the distinguished front and rear parts of each of the feet;
   determining a size of a foot image having a predetermined design corresponding to the specified size of each of the feet;
   mapping the foot image having the determined size to coincide with the specified position of each of the feet; and
   displaying the mapped foot image through the display.

7. The method according to claim 6, wherein
   the measured distribution of pressure applied to each of the feet is overlapped with the mapped foot image and the overlapped image is displayed through a display.

8. The method according to claim 6, wherein the step of generating the image data comprises:
   receiving values measured by pressure sensors in a state in which the user stands on the pressure sensor plate; and
   generating data of a grayscale image corresponding to the values measured by the pressure sensors.

9. The method according to claim 6, wherein the specifying step comprises:
   setting a check box at a contour of the image data set on the basis of the center line and specifying the size of each of the feet using a size of the check box;
   distinguishing between a front part and a rear part of each of the feet using opposite ends of the generated image data set through which the center line passes; and
   analyzing a distribution of data in the distinguished rear part of each of the feet to specify a heel region of each of the feet of the user.

10. The method according to claim 9, wherein the mapping step comprises:
    extracting a center point of the specified heel region of each of the feet of the user, adjusting a center point of a heel region of the foot image having the determined size so as to correspond to the extracted center point of the heel region of each of the feet of the user, and adjusting a center line of the foot image having the determined size so as to correspond to a center line of the extracted data set, thereby mapping the foot image having the determined size.

11. The method according to claim 6, further comprising finely adjusting the position of the mapped foot image based on the information regarding the distribution of pressure applied to each of the feet of the user overlapped thereon.

* * * * *